United States Patent [19]

Rutter

[11] Patent Number: 4,859,465
[45] Date of Patent: Aug. 22, 1989

[54] VACCINE CAPABLE OF ELICITING MULTIVALENT ANTIBODIES

[75] Inventor: William J. Rutter, San Francisco, Calif.

[73] Assignee: The Regents of the University of California, Oakland, Calif.

[21] Appl. No.: 139,171

[22] Filed: Dec. 21, 1987

Related U.S. Application Data

[63] Continuation of Ser. No. 602,432, Apr. 20, 1984, abandoned, which is a continuation of Ser. No. 213,881, Dec. 8, 1980, abandoned.

[51] Int. Cl.[4] .......................... C07K 15/00; C07K 9/00; C12N 15/00; A61K 39/12
[52] U.S. Cl. ...................................... 424/89; 530/350; 530/806; 435/172.3; 514/12
[58] Field of Search .................. 435/172.3; 424/89; 530/350, 806; 514/12

[56] References Cited

U.S. PATENT DOCUMENTS

| | | | |
|---|---|---|---|
| 4,366,246 | 12/1982 | Riggs | 435/317 |
| 4,400,376 | 8/1983 | Sanderson | 424/88 |
| 4,411,994 | 10/1983 | Gilbert et al. | 435/172.3 |
| 4,415,491 | 11/1983 | Vyas | 260/112.5 R |

OTHER PUBLICATIONS

Mulligan et al., Mol. Cell. Biol., vol. 14, pp. 643–654 (1979).
Natvig et al. The Journal of Immunology, vol. 112, pp. 1277–1284, (1974).
Mulligan et al., Chemical Abstract 92:125906f of ICN-UCLA Symp. Mol. Cell. Biol. (1979).
Peterson et al., PNAS U.S.A. vol. 74, pp. 1530–1534, Apr. 1977.
Goeddel et al., Nature, vol. 281, pp, 544–548, Oct. 1979.
Mercerou-Puijolon et al., Nature, vol. 275, pp. 505–510, Oct. 1978.
Helling et al., Genetic Engineering, CRC Process Inc, pp. 1,10–23 and 29 (1978).
Pasek et al., Nature, vol. 282, pp. 575–579, Dec. 6, 1979.
Budkowska et al., The Journal of Immunology, vol. 123, pp. 1415–1416, Sep. 1979.

Primary Examiner—Alvin E. Tanenholtz
Attorney, Agent, or Firm—Irell & Manella

[57] ABSTRACT

The present invention discloses a DNA transfer vector comprising two or more deoxynucleotide sequences coding for different antigenic materials linked together in phase with one another. The present invention further discloses the expression of said deoxynucleotide sequences either directly or as a fusion protein with the product of a procaryotic gene. The resulting expression product is then either a fusion protein comprising two or more antigenic materials or a fusion protein comprising a part of a procaryotic protein and two or more antigenic materials. These fusion products are capable of eliciting the formation of multivalent antibodies which are cross-reactive with any and all of the native antigenic material. A vaccine is also described utilizing these fusion products.

4 Claims, No Drawings

VACCINE CAPABLE OF ELICITING MULTIVALENT ANTIBODIES

This application is a continuation of application Ser. No. 602,432, filed Apr. 20, 1984 abandoned which is a continuation of application Ser. No. 213,881, filed Dec. 8, 1980, abandoned.

BACKGROUND OF THE INVENTION

Recombinant DNA technology has many potential uses. One use which is presently emerging is to utilize the protein products to prepare vaccines. This procedure involves the insertion of a DNA sequence coding for an antigenic substance into a transfer vector, transforming microorganism with this transfer vector and expressing the DNA sequence either directly or as a fusion protein. The protein product produced by the microorganism is antigenic and is capable of eliciting antibodies which are cross-reactive with the native antigen. Thus, the protein product can be administered as a vaccine to provide immunological protection against the native antigen. This aspect of recombinant DNA technology is particularly important in those cases where it is difficult to isolate enough antigenic material to prepare sufficient quantities of antibodies. Transformed microorganisms will be able to produce large quantities of antigenic material so that it will be practical to prepare vaccines for many additional diseases. An example of this particular technology is described in European Patent Application No. 0013828. This application describes the cloning of the Hepatitis B virus and demonstrates the ability of the expression products to elicit formation of antibodies in rabbits. Thus, it is possible to use the expression products of the cloned virus in a vaccine. Similarly, S. Cohen, in a letter to Nature (288, 8 (1980)), indicated that significant progress had been made in cloning the antigenic materials of malaria and that production of malaria vaccines was not far behind.

It has been recognized that many diseases, including viral infections, are characterized by the presence of more than one antigenic species. For example, the Hepatitis B virus has at least two antigenic materials—the core antigen and the surface antigen. Similarly, many pathogenic E. coli have two enterotoxins—one is heat labile and the other is heat stabile. Although the latter is not antigenic in itself, it is capable of acting as a hapten. It is well known that one antigen will only elicit antibodies that recognize that particular antigen. Consequently, vaccines containing one antigen will only produce antibodies towards that antigen. A vaccine having two or more antigens or a combination of two or more vaccines will produce a corresponding number of antibodies, but each antibody will be specific for only one antigen.

It is an object of the present invention to overcome this deficiency of prior art vaccines. The present invention provides for the preparation of a vaccine containing a fusion protein comprising two or more different antigenic materials. The fusion protein is expressed by microorganisms from a deoxynucleotide sequence which comprises two or more sequences, each coding for a different antigenic material, linked together in phase. The fusion protein elicits the formation of an antibody which is multivalent, i.e., the antibody is specific for each antigenic material. Consequently, the antibody can cross-react with any or all of the native antigenic materials and thus provide better protection, since the vaccine is directed to several antigenic materials. As used herein, antigenic material may refer to a substance which is antigenic per se or a substance which can act as a hapten. In addition, antigenic material as used herein refers to antigenic material exogenous to the host transfer vector or expression vector into which the antigenic material is inserted.

SUMMARY OF THE INVENTION

The present invention discloses a DNA transfer vector comprising two or more deoxynucleotide sequences coding for different antigenic materials linked together in phase with one another. The present invention further discloses the expression of said deoxynucleotide sequences either directly or as a fusion protein with the product of a procaryotic gene. The resulting expression product is then either a fusion protein comprising two or more antigenic materials or a fusion protein comprising a part of a procaryotic protein and two or more antigenic materials. These fusion products are capable of eliciting the formation of multivalent antibodies which are cross-reactive with any and all of the native antigenic material. A vaccine is also described utilizing these fusion products.

DETAILED DESCRIPTION OF THE INVENTION

The first step in preparing a vaccine in accordance with the invention is the synthesis of a deoxynucleotide sequence coding for a fusion protein having as its amino acid sequence the amino acid sequences of two or more antigenic materials. This DNA sequence, termed herein a linked DNA sequence, comprises two or more deoxynucleotide sequences each coding for a separate and different antigenic material. It is important that two or more deoxynucleotide sequences be linked together in phase so that the antigenic materials when expressed as a fusion protein will have the correct amino acid sequences. The linked deoxynucleotide sequence is prepared using conventional techniques.

In general, the individual DNA sequences coding for the antigenic materials are isolated or prepared by conventional techniques. For example, if the DNA sequences have previously been cloned into transfer vectors, they can be removed by digestion with the appropriate restriction endonucleases and purified by standard techniques. If the DNA sequences have not previously been cloned, they can be prepared in any conventional manner, such as by the cDNA method, by the isolation of DNA from the genetic material and the like. These sequences could be used directly or preferably first inserted into a transfer vector, and then characterized. If the sequences are inserted into a transfer vector, they are removed as described above.

When the two or more individual DNA sequences are linked together, it is important that only the last DNA sequence contains a stop codon. In other words, no stop codons should be present in the other DNA sequences. This can be accomplished by any one of several conventional techniques. For example, the stop codon and some surrounding nucleotides can be removed by digestion with a restriction endonuclease. A particular restriction endonuclease is selected based on the restriction sites available on the 5' side of the stop codon in the predetermined DNA sequence. If the restriction site is located too far upstream from the stop codon, it may be desirable to restore a portion of the DNA sequence. This can be accomplished, for example, by synthesizing the desired sequence by the phosphotriester method as described by Itakura, K., et al, *J. Biol. Chem.*, 250, 4592 (1975), and Itakura, K., et al, *J. Am. Chem. Soc.*, 97, 7326 (1975), or other suitable synthetic means. This synthesized DNA sequence can then be blunt-end ligated to the restriction endonuclease digested DNA sequence as described by Valenzuela, P., et al, *Nature*, 280, 815 (1979), resulting in a DNA sequence coding for most of an antigenic material but lacking the stop codon. Alternatively, the stop codon can be removed by digesting the DNA sequence by a restriction endonuclease which has a site on the 3' side of the stop codon. This stop codon is then removed from this product by controlled digestion of the 3' end using 3' exonuclease or T4 DNA polymerase, as described in copending application Ser. No. 125,878, filed Feb. 29, 1980, incorporated herein by reference, and then digesting the single stranded area of the DNA sequence with S1 nuclease.

After the stop codon has been removed from the necessary DNA sequences coding for the antigenic materials, the DNA sequences are then linked together. This linkage is done using conventional techniques. For example, if a common restriction site exists at the appropriate ends of the DNA sequences, the sequences can be cut by the restriction endonuclease and joined following the procedure described by Ullrich, A., et al, *Science*, 196, 1313 (1977). Alternatively, the DNA sequences can be linked together by the method of blunt-end ligation as described by Valenzuela, P., et al, supra. A third possible method involves the blunt-end ligation of restriction linkers onto the DNA sequences, digestion with the restriction endonuclease and ligation of the sequences. Any combination of these methods is also possible. Modifications of any of the sequences to be linked together by one or two nucleotides in order to achieve correct reading frame phase are well known in the art. Thus, a linked DNA sequence is obtained wherein the individual DNA sequences each coding for a different antigenic material are linked together in phase. The linked DNA sequence is then isolated and purified by standard techniques.

The purified linked DNA sequence is then inserted into a transfer vector or expression vector using conventional techniques. For example, the linked DNA sequence can be inserted into appropriate sites within expressed operons, including, for example, the Pst I site in the β-lactamase gene of pBR322 (VillaKomaroff, L., et al, *Proc. Nat. Acad. Sci. U.S.A.*, 75, 3727 (1978) and Seeburg, P., et al, *Nature*, 274, 795 (1978)), the EcoRI site of PBR322 carrying the lac control region and coding sequence for β-galactosidase (Itakura, K., et al, *Science*, 198, 1056 (1977)) or the HindIII site of the trpD gene of plasmid ptrpED50 (Martial, J., et al, *Science*, 205, 602 (1979)). Modifications of sequence length, if needed, by one or two nucleotides in order to achieve correct reading frame phase are well known in the art. Upon expression, a fusion protein is obtained which comprises a portion of the procaryotic protein as the N-terminal end and the amino acid sequence coded for by the linked DNA sequence as the C-terminal end. Alternatively, the linked DNA sequence can be inserted into a direct expression vector. That is, the expression product is not the fusion protein described above, but only the amino acid sequence coded for by the linked DNA sequence. For example, the linked DNA sequence can be inserted into the Cla I site of the direct expression vector ptrpL1 as described in copending application Ser. No. 213,879 filed Dec. 8, 1980, incorporated herein by reference.

Alternatively, a transfer vector containing a linked DNA sequence can be prepared by utilizing any combination of the above-described procedures. For example, a transfer vector or expression vector containing a deoxynucleotide sequence coding for one antigenic material can be cut by a restriction endonuclease upstream from the stop codon, thus opening up the vector. A second deoxynucleotide sequence coding for a different antigenic material can be isolated and nodified as discussed above. This second DNA sequence can then be inserted into the opened vector as described above. The resulting vector would then contain a linked DNA sequence comprising two DNA sequences each coding for a different antigenic material.

After the transfer vector or expression vector containing the linked DNA sequence has been prepared, a suitable microorganism, for example, host bacterial such as *E. coli* χ1776, RR1 or HB101 or other bacteria are transformed by conventional techniques. Transformants are then grown under conditions suitable for expression of the linked DNA sequence. The protein product produced by expression can be either a fusion protein comprising the amino acid sequences of two or more antigenic materials or a fusion protein comprising a portion of a procaryotic protein as the N-terminal end and as the C-terminal end a fusion protein comprising the amino acid sequences of two or more antigenic materials. The protein product is isolated and purified using conventional techniques, including for example, gel filtration and affinity chromatography.

The purified protein product is examined for its capability of eliciting the formation of an antibody which is crossreactive with all of the native antigenic materials corresponding to the protein product. Since the antibody preparation would be capable of binding several antigens, it may provide better protection against a particular disease. A vaccine containing the purified protein product is prepared by conventional techniques.

The details of the present invention will be further described by the following examples. In these examples, digestions with restriction endonucleases were carried out under conditions optimized for each enzyme. Restriction endonucleases, their nomenclature and site specificity, have been described in detail by Roberts, R., *Nucleic Acids Res.*, 8, r63–r80 (1980). Enzymes were obtained commercially (New England BioLabs, Cambridge, Mass.) and optimal conditions according to supplier's recommendations were employed unless noted otherwise. T4 DNA ligase was obtained from New England BioLabs. The use of T4 DNA ligase and suitable reaction conditions have been previously described by Valenzuela, P., et al, supra, and Ullrich, A., et al, supra. Micrococcal S1 nuclease was obtained from Miles Laboratories, Elkhart, Ind. The use of S1 nuclease and suitable reaction conditions have been previously described by Ullrich, A., et al, supra.

EXAMPLE 1

This example describes the linking of the Hepatitis B core antigen (HBcAg) gene and the Hepatitis B surface antigen (HBsAg) gene in phase.

Double-stranded circular HBV-DNA was obtained from Dane particles containing 25 μg DNA, as described by Hruska, J. F. et al., *J. Virol.* 21, 666 (1977). The DNA was initially screened for sensitivity to restriction endonucleases by gel electrophoresis of the products of enzymic digestion. Gel electrophoresis fractionates nucleic acids according to their molecular length, Helling, R. et al., *J. Virol.* 14, 1235 (1974). Treatment of 100 ng DNA with EcoRI endonuclease (2 units) resulted in a single sharp band corresponding to about 3200 base pairs (bp) length. Similar treatment with BamHI endonuclease resulted in two fragments corresponding to about 1200 and 2000 bp length. Restriction endonucleases were obtained from New England BioLabs, Beverly, Mass. Units are defined by the manufacturer. All reactions using restriction endonucleases were carried out in buffers recommended by the manufacturer. From the number of fragments obtained in each case, it was inferred that HBV-DNA contains a single EcoRI site and two BamHI sites.

The DNA transfer vector selected was the plasmid pBR325 (Bolivar, F. *Gene* 4, 121 (1978), which is derived from plasmid pBR322 (Bolivar, F. et al., *Gene* 2, 95 (1977) and is capable of transforming *E. coli.* Plasmid pBR 325 carries a gene conferring chloramphenicol resistance ($Cm^r$) and ampicillin resistance ($Ap^r$) on transformed cells. An EcoRI site exists in the $Cm^r$ gene such that an insertion of exogenous DNA at the EcoRI site renders the $Cm^r$ gene inoperative while leaving the $Ap^r$ gene unaffected. Recombinant clones of transformed *E. coli* are identified as chloramphenicol sensitive and ampicillin resistant, while non-transformed cells, sensitive to both chloramphenicol and ampicillin, fail to grow in the presence of either antibiotic. Clones transformed with non-recombinant pBR325 are identified as chloramphenicol resistant and ampicillin resistant. The microbiological methods used for growth and selection of recombinant strains were standard methods, described in *Experiments in Molecular Genetics* by Jeffrey H. Miller, Cold Spring Harbor Laboratory (1972).

For the insertion process, purified pBR 325, 50 ng, and 300 ng HBV-DNA were first treated together with EcoRI endonuclease, 10 units (10 µl total vol.) at 37° C. for one hour to yield linear plasmid DNA. The reaction mixture was heated to 65° C. for five minutes to inactivate EcoRI endonuclease.

The DNA was isolated from the reaction mixture by two cycles of ethanol precipitation. The precipitate was resuspended in 10 µl $H_2O$ to which a buffer concentrate was added to give 50 mM tris-HCl pH 8.0, 1 mM ATP, 10 mM $MgCl_2$ and 20 mM dithiothreitol. The mixture was pretreated by incubation at 37° C. for five minutes, followed by five minutes at room temperature. The mixture was then cooled in an ice bath and incubated with 1 unit T4 ligase (P-L Biochemicals, 11,000 units/ml) at 14° C. for 15 hours. The reaction mixture was added directly to a suspension of *E. coli* cells prepared for transformation by standard techniques. The host cell strain chosen was *E. coli* HB101, described by Boyer, H. W. and Rolland-Dussoix, D. *J. Mol. Biol.* 41, 459–472 (1969). The choice of a particular strain was based upon convenience. Strain HB101 contains no other plasmids, is sensitive to chloramphenicol and to ampicillin and it is relatively easy to grow and maintain stocks of the organism.

Single colonies of transformed cells containing a recombinant plasmid, as judged by chloramphenicol sensitivity and ampicillin resistance, were grown in culture to provide a source of plasmid DNA. Cultures were grown in L-broth at 37° C. with aeration and harvested in late log or stationary phase. Alternatively, transformed cells were grown in a suitable minimal medium, as described by Bolivar, F. et al., *Gene* 2, 95 (1975) and Bolivar, F. *Gene* 4, 121 (1978) to an optical density at 660 nm of 1.0, using a 1 cm cuvette. Chloramphenicol, 170 µg/ml, as then added and the culture was incubated overnight. In either case, the plasmid DNA was isolated as supercoils from a cell lysate, using the method of ethidium bromide CsCl density gradient centrifugation described by Clewell, D. B. and Helinsky, D. R., *Proc. Nat. Acad. Sci. U.S.A.* 62, 1159 (1969). Plasmid DNA prepared from transformed cells was treated with EcoRI endonuclease and fractionated by gel electrophoresis, as described. Single colonies were screened by the toothpick assay described by Barnes, W. M., *Science* 195, 393 (1977), to identify those bearing plasmids with large inserts. Two independently isolated recombinant plasmids containing insertions about 1200 bp in length were selected for subsequent studies. These were designated pEco-3 and pEco-63.

A recombinant clone containing the entire Hepatitis B virus DNA, as described by Valenzuela, P., et al, supra, Valenzuela, P., et al, *Animal Virus Genetics,* Fields, B., et al, Eds., Academic Press, New York, N.Y., and copending application Ser. No. 107,267, filed Dec. 21, 1979, incorporated herein by reference, was digested with HincII. A 744 base pair fragment containing the coding sequence for all of HBsAg except for about 22 amino acids of the N-terminal end was isolated by gel electrophoresis. The lacking amino acids are believed to be the signal peptide which is normally cleaved during translation.

Hepatitis B core antigen (HBcAg) gene was inserted into the expression vector ptrpL1 in order to demonstrate direct expression of a foreign gene.

A recombinant clone containing the entire hepatitis B virus DNA, as described by Valenzuela, P. et al., *Nature* 280, 815 (1979) and Valenzuela, P. et al., *Animal Virus Genetics,* Fields, B., Janenisch, R., and Fox, C. F., Ed., Academic Press, N.Y., 1980, was digested with HhaI. A 1005 base pair fragment containing the HBcAg gene was isolated by preparative acrylamide gel electrophoresis. 20 µg of the HhaI fragment were treated with HpaII methylase as described by Yoo, J. and Agarwall, K. L., *J. Biol. Chem.* 255, 6445 (1980). The fragment was then treated with 28 units of T4 DNA polymerase in the absence of deoxynucleotide triphosphates in 30 mM Tris-acetate, 67 mM K-acetate, pH 7.8, 10 mM Mg-acetate, 0.5 mM dithiothreitol, and 100 µg/ml bovine serum albumin for 30 seconds at 37° C. in order to remove nucleotides from the 3' ends. This reaction produced fragments containing the HBcAg gene and having 5–20 base pairs separating the end of the fragments and the start codon. The reaction was stopped by the addition of phenol. The DNA was extracted with chloroform: isoamyl alcohol (24:1) and precipitated with ethanol. The resulting fragment was then treated with S1 nuclease and BamHI linker molecules (d(pCCGGATCCGG)) ligated thereto as described by Ulrich, A. et al., *Science* 196, 1313 (1977). The BamHI linker treated fragment was cut with HpaII, the mixture extracted with phenol-chloroform and precipitated with ethanol. The fragment containing the HBcAG gene was purified from the digested linkers by preparative acrylamide gel electrophoresis. The plasmid ptrpLI was cut with ClaI, treated with alkaline phosphatase and the fragment inserted therein following the procedure described by Ulrich, A., et al., *Science* 196, 1313 (1977). Host bacteria HB101 were transformed by the resulting recombinant vector bearing the HBcAg gene.

Transformants were selected on L plates (Miller, J. H., in *Experiments in Molecular Genetics,* Appendix I, Cold Spring Harbor Laboratory, Cold Spring Harbor, N.Y., (1972)) containing 20 μg/ml ampicillin and screened for recombinants using a modified toothpick assay (Barnes, W. B., *Science* 195, 393 (1977)). Forty such recombinants were then tested for HBcAg using a double antibody radioimmune assay with human anti-HBcAg (Ling, C. M. and Overbey, L. R., *J. Immunol.* 109, 834 (1972)). Seventeen of these recombinants were positive for HBcAg. Restriction enzyme analysis of the plasmids showed that all seventeen contained the HBcAg gene sequence and all were in proper orientation for trp-dependent expression of HBcAg. Four of these plasmids were analyzed by DNA sequence analysis. It was found that the distance between the leader ribosomal binding site and the start codon of the HBcAg gene varied from 12–15 base pairs. The plasmid producing the highest level of HBcAg was identified as ptCA 246.

A recombinant clone containing the entire HBcAg gene linked to the trp promoter and leader ribosomal binding site (ptCA 246), as described by copending application Ser. No. 213,879 filed Dec. 8, 1980, incorporated herein by reference, was digested with Ava I. Two restriction sites exist within ptCA 246 for Ava I. One of these is upstream from the stop codon. Insertion of a second DNA sequence at this point eliminates the stop codon and nucleotides coding for six amino acids of the C-terminal end of HBcAg. Since there are two restriction sites for Ava I, digestion with Ava I results in four possible products, two of which are full-length linear DNA fragments. One of these latter two has been cut at the Ava I site within the HBcAg gene. The full-length linear DNA fragments were isolated by gel electrophoresis and digested with S1 nuclease to provide blunt ends as described by Ullrich, A., et al, supra. The S1 nuclease treated fragments were then treated with alkaline phosphatase as described by Ullrich, A., et al, supra.

The 744 base pair HBsAg fragment was blunt-end ligated to the full-length DNA fragments prepared above by the procedure described by Valenzuela, P., et al, supra. Host bacteria HB101 were transformed by the resulting recombinant vector bearing the HBcAg and HBsAg genes linked together. Transformants were selected on L plates (Miller, J. H., *Experiments in Molecular Genetics,* Appendix I, Cold Spring Harbor Laboratory, Cold Spring Harbor, N.Y. (1972)) containing 20 μg/ml ampicillin and screened for recombinants using a modified toothpick assay (Barnes, W. B., *Science,* 195, 393 (1977)).

Overnight cultures of the ampicillin-resistant transformants were prepared in M9 media (Miller, J. H., supra) containing 0.25% casamino acids, 0.5% glucose and 0.01% B1. The cultures were diluted 1:10 with fresh media, grown for one hour at 30° C., 15 μl of 3β-indolylacrylic acid was added, and the cultures grown for another two hours at 30° C. Cultures in which 3β-indolylacrylic acid was not added or cultures containing the plasmid ptripL1 were used as the controls. The cultures were then labeled for 20 minutes at 30° C. with 100 μCi/ml of $^{35}$S-cysteine. The protein products were electrophoresed on sodium dodecylsulfate-polyacrylamide gels and the protein bands were visualized by autoradiography. One clone, identified as ptC/SA, was found which produced a new protein having the predicted weight for a fusion protein containing the HBcAg as the N-terminal end and HBsAg as the C-terminal end.

Cells were grown and labeled with $^{35}$S-cysteine as described above. The labelled cells were collected by centrifugation and resuspended in phosphate-buffered saline containing 1 mM phenylmethylsulfonylfluoride. The cells were sonicated and proteins immunoprecipitated with anti-HBsAg serum, antiHBcAg serum or normal IgG as the control using the SAC technique described by Martial, J. A., et al, *Science,* 205, 602 (1979). The new protein band seen above was found to be immunoprecipitated by both anti-HBsAg serum and anti-HBcAg serum. These results clearly show that a fusion protein containing HBcAg and HBsAg is produced by transformed cells.

EXAMPLE 2

The HBcAg - HBsAg fusion protein is sufficiently antigenic to elicit antibodies which are cross-reactive with native HBsAg and native HBcAg. The HBcAg - HBsAg fusion protein expressed as described in Example 1 is purified from cell lysates using conventional techniques, including among others, gel filtration and affinity chromatography. Guinea pigs are injected subcutaneously at 9, 14 and 56 day intervals with 10 ml physiological saline or phosphate-buffered saline containing 500 μg of the purified HBcAg - HBsAg fusion protein. The serum of the test animals is sampled at 0, 28, 56 and 84 days and assayed for antibody titre against Dane particles HBcAg or HBsAg partially purified from infectious serum. The radioimmunoassay of Hollingren, F., et al, *J. Immunol.,* 107, 1099 (1971) is employed. The majority of animals exhibit antibodies cross-reactive with the Dane particle and both HBcAg and HBsAg 84 days after administration of the protein. Similar results are obtained upon injection of monkeys. Accordingly, the immunologically active protein constituent of Hepatitis B virus, expressed by a microorganism that has been transformed by a DNA transfer vector encoding HBcAg - HBsAg, is capable of eliciting antibodies cross-reacting with both immunologically reactive components of the virus.

The described HBcAg - HBsAg fusion protein has the advantage of containing both antigens of Hepatitis B virus such that a multivalent antibody cross-reactive with both native HBcAg and native HBsAg is formed upon vaccination. Furthermore, there is no danger of accidental infection since there is no intact virus in the HBcAg - HBsAg expression product. By contrast, viral proteins purified from serum always pose the danger of viral contamination.

Since this fusion protein is capable of eliciting antibodies cross-reactive with native HBsAg and HBcAg, it therefore follows that the purified fusion protein administered in physiologically acceptable medium constitutes a vaccine for protection against infection by the Hepatitis B virus.

Sixteen chimpanzees are divided into three groups. Group A (6 animals) is inoculated intravenously with 1.0 ml of B.O.B. Hepatitis B virus; Group B (4 animals) is inoculated intravenously with 1.0 ml containing 5 mg of the purified HBcAg - HBsAg fusion protein in physiological saline; Group C (6 animals) is the control group and receives no inoculation. All chimpanzees in Group A have evidence of clinical Hepatitis B (either antigenemia, enzyme elevations and/or antibody response) within forty weeks. None of the animals in Groups B or C shows evidence of clinical Hepatitis B infection over the same 40-week period. The chimpanzees of Group B are rendered immune to subsequent challenge when inoculated intravenously with 1.0 ml of B.0.B. Hepatitis B virus.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A fusion protein for use in a multivalent hepatitis b vaccine comprising antigenic determinants derived from at least two proteins encoded by the hepatitis B genome,
   wherein the encoded proteins are hepatitis B core antigen and hepatitis B surface antigen,
   wherein said fusion protein is capable of eliciting the formation of antibodies which are immunoreactive with each of said proteins.

2. The fusion protein according to claim 1 further comprising a procaryotic peptide segment.

3. A vaccine comprising a sterile, physiologically acceptable diluent and the fusion protein of claim 1 as the active ingredient.

4. A method to immunize subjects against infection by hepatitis B which comprises administering to a subject in need of such immunization an effective amount of the vaccine of claim 3.

* * * * *